United States Patent [19]

Meyer

[11] Patent Number: 5,017,135
[45] Date of Patent: May 21, 1991

[54] TRAP AND SEPARATOR FOR DENIAL VACUUM SYSTEMS

[75] Inventor: Robert A. Meyer, Spearfish, S. Dak.

[73] Assignee: Ramvac Corporation, Spearfish, S. Dak.

[21] Appl. No.: 423,234

[22] Filed: Oct. 18, 1989

[51] Int. Cl.$^5$ .............................................. A61C 17/06
[52] U.S. Cl. .................................................... 433/92
[58] Field of Search ................. 433/91, 92, 97; 4/263, 4/264, DIG. 19; 55/421, 429; 137/171, 177

[56] References Cited

U.S. PATENT DOCUMENTS

| | | | |
|---|---|---|---|
| 665,571 | 1/1901 | Metzler | 433/92 |
| 3,484,941 | 12/1969 | Svard | 433/92 |
| 3,777,403 | 12/1973 | Ritchie | 433/92 |
| 3,964,112 | 6/1976 | Plowman | 433/97 |
| 3,988,134 | 10/1976 | Gandrud | 433/92 |
| 4,529,383 | 7/1985 | Jerzy | 433/92 |

*Primary Examiner*—John J. Wilson
*Attorney, Agent, or Firm*—Nixon & Vanderhye

[57] ABSTRACT

A dental vacuum system includes a sludge trap and liquid separator between dental operatories and a vacuum source (vacuum pump). The sludge trap separates out metals, such as silver, gold, and mercury, and other large particles from the fluid flow between the operatories and the vacuum source. By utilizing a static structure including a sanitary tee, a plastic pipe extending downwardly from the tee, and a slide valve, the metals may be easily collected, and periodically capped and sent to salvage, for the recovery of the metals. The liquid separator comprises a number of plastic pipes extending downwardly from a linear flow path of the fluid slurry to the vacuum pump. A number of sanitary tees are provided connected to the pipes, the pipes each having a larger cross-sectional area (diameter) than the fluid conduit connected to the vacuum pump. At their bottoms, the pipes are connected to a common drain valve. No-hub (quick release) couplings may be used for easy removal of components.

14 Claims, 2 Drawing Sheets

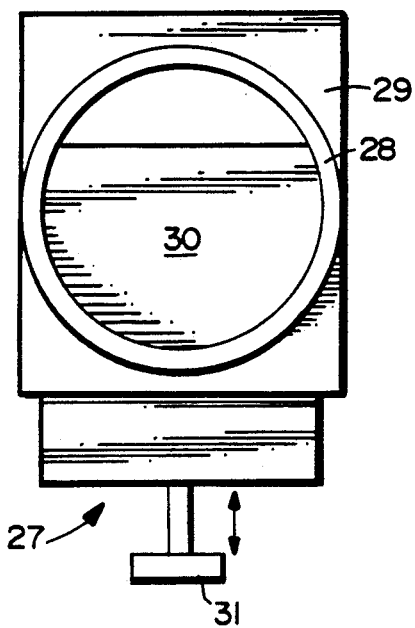
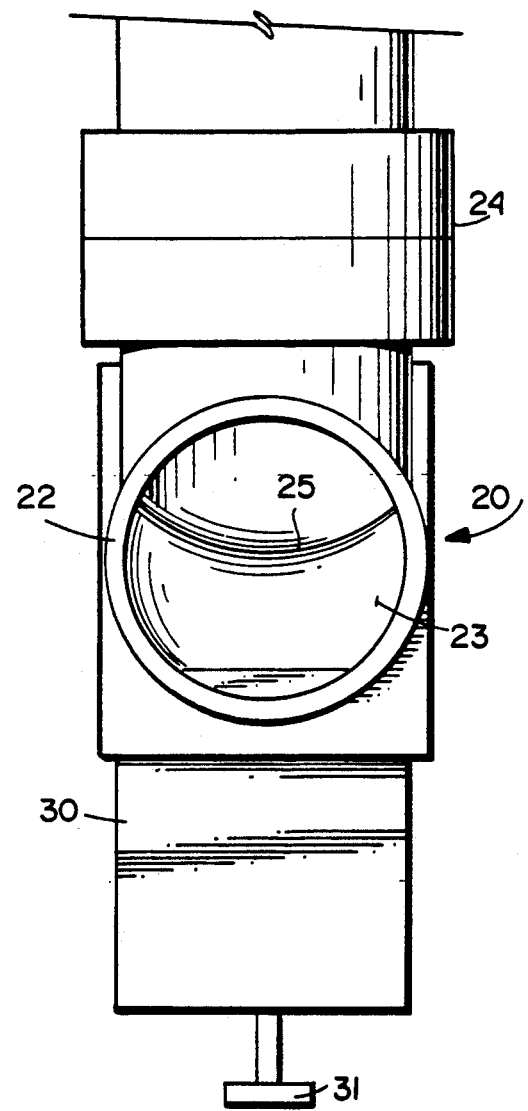
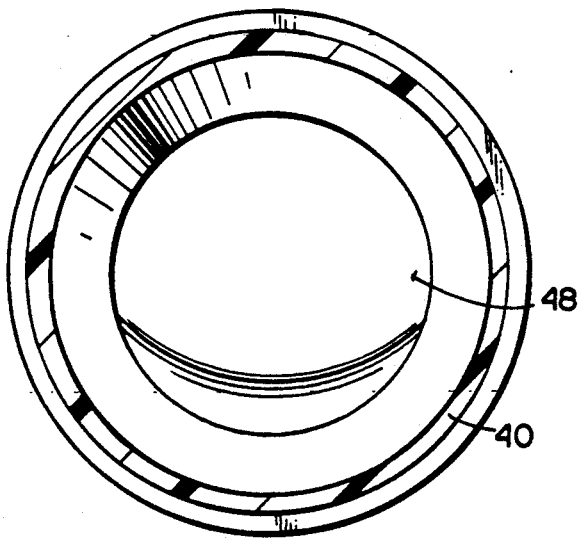

TRAP AND SEPARATOR FOR DENIAL VACUUM SYSTEMS

BACKGROUND AND SUMMARY OF THE INVENTION

In dental offices, central vacuum systems are conventionally used to transport materials away from the dental chairs, for disposal. Materials typically transported include gases, aerosols, liquids, slurries, and solid particulates. The gases flow completely through the system to the vacuum source and are exhausted from the vacuum source. However the liquids, slurries, particulate solids, and the like desirably are removed from the system before the vacuum source. Liquid ring (water ring) vacuum pumps can pass both liquids and slurries to a sewage line while large particle sized solids are trapped by a filter (which is serviced periodically), but for other types of vacuum pumps it is necessary to prevent the liquids, slurries and solid particulates from entering the pump.

In typical dental vacuum systems having non-liquid ring type vacuum pumps, liquid and small particle separation is provided by a separator tank. Typically the flow of fluid from the dental operatories passes into the top of the tank, which has a much larger cross-sectional area than the conduit transporting the fluid slurry, and the liquids and particles fall to the bottom of the tank. Periodically the contents of the tanks are emptied into a sewage line.

In all types of conventional dental vacuum systems, some of the slurry particles travelling from the operatories to the vacuum source settle on the bottom of the pipes or other equipment. Occasionally, large chunks of settled debris break loose and become lodged in filters, separating devices, or drain valves. This causes a very significant problem and may result in the break down of the entire vacuum system. Significantly, the particles being transported in the vacuum system, especially the larger particles, also pose a potential pollution problem since they contain metals including silver amalgam (which is primarily silver and mercury), gold, and other precious and semi-precious metals. Not only are these metals a potential significant pollution source, but they have real value and if salvaged can defray system operating costs.

According to the present invention, a dental vacuum system is provided which has a sludge trap means which allows larger particulates, which includes a great deal of metal, from the vacuum source to be collected so that they need not be filtered out or separated out with liquids in a conventional liquid and slurry separator. The sludge trap according to the invention comprises a simple basically static structure which collects the separated metals and allows them to be periodically removed from the system and sent to a salvage facility so that the metals can be recovered. The sludge trap means according to the invention comprises a simple sanitary tee connected at a downwardly extending in-line outlet to a downwardly extending, closed end trap element, preferably a piece of plastic pipe capped at its opposite end. A valve, such as a slide valve, is provided between the sanitary tee and the pipe, and the pipe is connected to the valve by a coupling means, such as a no-hub (quick release) coupling. The sludge trap according to the invention can be used with any vacuum source, is easy to utilize to capture the salvageable material, and provides a container for the salvageable material that may be directly shipped to a salvage facility, is inexpensive and easy to install, and is "fail safe". Unlike a filter, if the sludge trap according to the invention is not emptied and becomes filled to capacity, it will not clog the vacuum line any more than if it were not present at all.

While the sludge trap according to the invention may be used alone in any conventional vacuum system, in non-liquid ring pump systems it is preferably utilized with a particular liquid separating means according to the invention. The liquid separating means is disposed in the fluid line between the dental operatories and the vacuum source downstream of the sludge trap. The liquid separator according to the invention comprises a plurality of downwardly extending tubes, preferably plastic pipes, each having a larger cross-sectional area than the cross-sectional area of the vacuum conduit. The downwardly extending pipes are connected to the elbow of a sanitary tee so that the liquid and smaller particles will move downwardly into the pipes while the gases continue to flow through the in-line conduit formed by the sanitary tees. A common drain is provided at the bottom of the downwardly extending tubes to allow periodic draining of the liquid and collected slurry materials within the separator. While the liquid separator according to the invention is preferably utilized with the sludge trap of the invention, it can be used without the sludge trap too in place of any conventional tank liquid separator.

The liquid separator according to the invention also have a number of advantageous features. It can be used with any vacuum source, and effectively achieves separation while it saves space compared to tank separators. For example it can be wall mounted and extends away from the wall mounting surface only a matter of a few inches. It can easily be custom made in a wide variety of sizes, and is readily constructed from off the shelf plumbing components. The drain may easily be removed for inspection and cleaning, and the drain valve associated with it is kept closed by vacuum, and has a large opening. Therefore if it clogs it tends to "fail safe", in an open position.

The invention also relates to a sludge trap per se, a method of recovering metals from the fluid slurry in a dental vacuum system, and a method of removing liquids and small particles from a fluid slurry in a dental vacuum system, utilizing the equipment as described above.

With respect to the method of recovering metals from a fluid slurry in a dental vacuum system, the method comprises the steps of: (a) Flowing a fluid slurry under the suction of the vacuum source from the operatories toward the vacuum source in a generally linear first flow path along at least a part of the distance between the operatories and the vacuum source. (b) Effecting a change in the direction of the fluid slurry while flowing in the first flow path to cause large particulates, including metals, in the fluid slurry to move downwardly out of the fluid slurry, while the fluid slurry, including any liquid or smaller particles therein, continues in a second flow path. (c) Collecting the separated out large particulates in a vessel below the first flow path. And (d) periodically capping the vessel, removing it from the dental vacuum system, and effecting recovery of the metals from the separated out particles therein.

The method of removing liquids and small particles from a fluid slurry in a dental vacuum system according to the invention comprises the steps of: (a) Flowing a fluid slurry under the suction of the vacuum source from the operatories toward the vacuum source in a generally linear first flow path along at least a part of the distance between the operatories and the vacuum source. (b) Providing a plurality of downwardly directed second flow paths from the first flow path, each of the second flow paths having a larger cross-sectional area than the first flow path, so that liquids and smaller particles will flow in one of the second flow paths while gases will continue to flow in the first flow path to the vacuum source. And, (c) periodically draining the liquids and smaller particles from all of the second flow paths at the same time.

It is the primary object of the present invention to provide for the effective separation of large particulates, including metals, liquids, and small particles, from a fluid slurry in a dental vacuum system, in an effective yet inexpensive and fail safe manner. This and other objects of the invention will become clear from inspection of the detailed description of the invention and from the appended claims.

BRIEF DESCRIPTION OF THE DRAWINGS

FIG. 2 is a top plan view looking down at the top of the valve of the sludge trap according to the invention;

FIG. 3 is a top plan view looking down at the top of the sanitary tee of the sludge trap according to the invention; and FIG. 4 is a longitudinal cross-sectional view of one of the tubular elements of the liquid separator of FIG. 1.

DETAILED DESCRIPTION OF THE DRAWINGS

Figure 1:
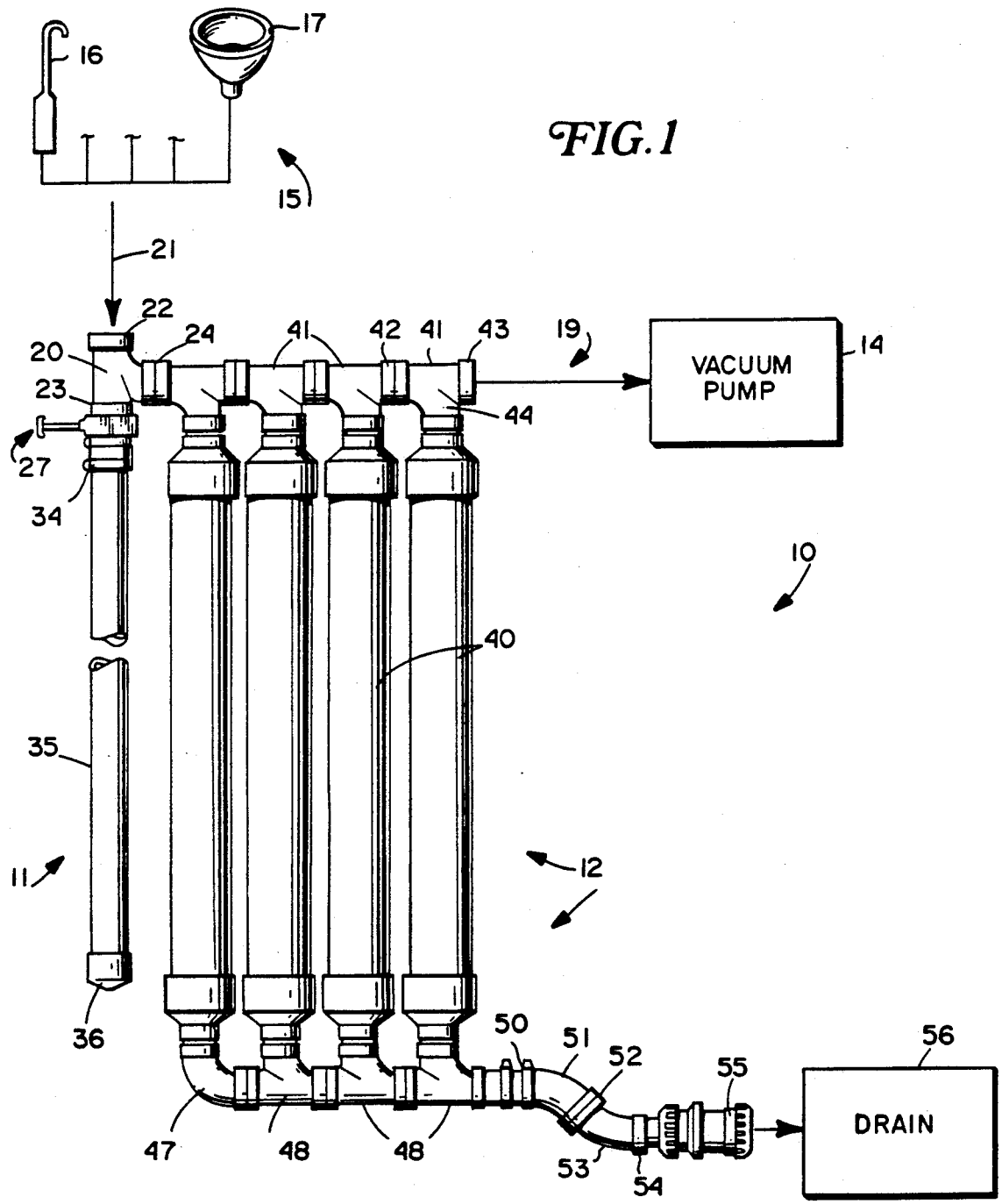
FIG. 1 is a side schematic view of a dental vacuum system utilizing a sludge trap and liquid separator according to the present invention.

A dental vacuum system in general is shown by reference numeral 10 in FIG. 1. It includes as the two major components according to the invention a sludge trap means 11 and a liquid separating means 12. The means 11, 12 are connected to a vacuum source which includes a vacuum pump 14 and may also include a vacuum reservoir or like conventional components. The vacuum pump may be of any type. The system 10 also includes a plurality of dental operatories shown generally by reference numeral 15, which may include saliva ejectors 16, cuspidor bowls 17, and the like. A fluid conducting line 19 operatively connects operatories 15 to the vacuum source and pump 14.

The sludge trap 11 according to the invention comprises a first conduit element 20. The first conduit element 20 preferably comprises a sanitary tee of PVC or ABS plastic such as can be purchased off the shelf in plumbing supply stores. The element 20 is operatively connected to the line portion 21 of the fluid conducting line 19, at an inlet 22 thereof. An outlet 23 is in line with the inlet 22, while an elbow outlet 24 makes an angle with respect to the inlet 22 (typically a right angle). The sludge trap means 11 also comprises a valve means 27 which preferably is a conventional slide valve which can be purchased from recreational vehicle plumbing supply stores. As illustrated in FIGS. 2 and 3, the valve means 27 includes an upper housing surface 28 which is connected to the in-line outlet 23 of the sanitary tee 20, a housing 29, and a slideable valve element 30 moved by actuator (handle) 31 manually between open and closed positions. FIG. 3 shows the valve element 30 in a completely open position, while FIG. 2 shows it in a partially open position. It can be moved to a completely closed position to entirely close off anything below the housing 29 from the fluid conducting line 19.

The sludge trap means 11 also comprises a coupling means 34 for coupling the valve means 27 to a downwardly extending, closed end, trap element 35. The coupling 34 may be a screw coupling, but preferably is a no-hub (quick release) coupling so that it may be easily detached and a new element 35 re-attached. The element 35 preferably comprises a length of plastic pipe (e.g. more than a foot long), such as PVC or ABS plastic circular cross-section (e.g. two inch diameter) pipe, having a PVC or ABS plastic end cap 36 at the bottom thereof. The open top of the pipe 35 receives large particulate solids and some slurries, as they "fall out" when the fluid flowing in the section 21 of line 19 is moved by the tee 20 from a first linear flow path to a second flow path substantially perpendicular to the first flow path, as the fluids in the flow path continue to flow toward the vacuum source 14.

The sludge trap 11 comprises an effective means for removing metals and like particular solids from the vacuum fluids in a dental vacuum system, and allows ready recovery of the metals. This is accomplished by flowing the fluid slurry under the suction of the vacuum source 14 in the first linear flow path 21, effecting a change in the direction of the fluid slurry using the sanitary tee 20 so that the fluids continue to flow in a second flow path through the elbow outlet 24 while the metals and other large particulates move downwardly into the pipe 35, collecting the large particulates in the pipe 35, and then periodically capping the pipe 35 by closing the valve 27, uncoupling the pipe 35 from the valve means 27 utilizing the no-hub coupling 34, and then putting a plastic cap on the top of the pipe 35. A new pipe 35 may then be put in place in association with the coupling 34 while the old pipe is shipped to a salvage facility for recovery of the silver, gold, mercury, and other metals therein. It will thus be seen that with essentially purely static structures the effective removal of metals from a dental vacuum system is accomplished in a simple and inexpensive manner, while a potential pollution problem is avoided and system costs can be defrayed by the valve of the recovered metals.

The liquid separating means 12 according to the present invention—when used in conjunction with the sludge trap 11—is connected downstream of the sludge trap 11 from the operatories 15. The liquid separator 12 comprise a plurality of generally vertically extending, generally parallel tubes 40 (e.g. four tubes 40). These tubes are preferably circular in cross-section, as illustrated in FIG. 4, and may be off the shelf pieces of PVC, ABS, or like plastic pipe. Each of the pipes 40 has a larger cross-sectional area (e.g. diameter) than the cross-sectional area of the fluid conducting line 19. For example if the line 19 at the point of the liquid separator 20 has a typical inside diameter of about two inches, the pipes 40 would have an inside diameter of about four inches. The pipe diameters are much smaller than those of a conventional liquid separator tank, however. The pipes 40 extend generally downwardly from the line 19.

The liquid separator 12 also comprises a plurality of sanitary tees 41 forming the line 19 at the point of the liquid separator 12. Each of the sanitary tees 41 has an inlet 42, an in line outlet 43, and an elbow outlet 44

(typically at an angle of about 90° with respect to the line between the inlet 42 and outlet 43). The elbow outlets 44 extend downwardly from the line 19 and may be connected to the tops of the pipes 40 by any suitable dual diameter couplings, including rigid or flexible couplings. At the bottoms, the tubes 40 are connected to a common drain. For example utilizing a plastic elbow 47 and a plurality of sanitary tees 48, the pipes 40 are connected through a no-hub coupling 50 to a drain 56.

Provided between the no-hub coupling 50 and the drain 56 are street 45° plastic pipe section 51, plastic bushing 52, street 45° plastic pipe section 53, PVC straight pipe 54, and a drain valve 55. The drain valve is a conventional large orifice size drain valve which may be readily disconnected—utilizing the no-hub coupling 50—from the rest of the liquid separator system 12. The bushing 52 and street 45°'s 51, 53 position the entire drain lower than the rest of the separator 12. This favors complete draining. The bushing 52 preferably reduces pipe size (e.g. 2" I.D. for 51, and 1.5" I.D. for 53) and is so located that the "step" associated with diameter reduction occurs on an incline rather than a horizontal run, and therefore does not impede free drainage.

Utilizing the separator 12 it is possible to remove liquids and small particles from a fluid slurry in a dental vacuum system by flowing the fluid slurry under the suction of the vacuum source 14 from the operatories 15 toward the vacuum source 14 in a generally linear first flow path (from inlets 42 to outlets 43); providing a plurality of downwardly directed second flow paths (elbow outlets 44 and pipes 40) from the first flow path, each second flow path (pipes 40) having a larger cross-sectional area (e.g. a diameter about twice as large) than the first flow path so that liquids and smaller particles will flow in one of the second flow paths while gases will continue to flow in the first flow path toward the vacuum source; and periodically draining the liquids and smaller particles from all of the second flow paths (pipes 40) at the same time by opening the drain valve 55. Periodically the drain valve 55 may be disconnected, using the no-hub coupling 50, for inspection, repair, and cleaning.

Both the sludge trap 11 and the liquid separator 12 according to the invention have numerous advantages, not the least of which is that they can be used With any vacuum source and will "fail safe". They are also static structures that are simple, inexpensive, and easy to construct, and the component parts are readily obtainable and replaceable.

While the invention has been herein shown and described in what is presently conceived to be the most practical and preferred embodiment thereof it will be apparent to those of ordinary skill in the art that many modifications may be thereof within the scope of the invention, which scope is to be accorded the broadest interpretation of the appended claims so as to encompass all equivalent structures and procedures.

What is claimed is:

1. A dental vacuum system including a source 5 of vacuum operatively connected by a fluid conducting line to a plurality of operatories, and comprising a sludge trap means located in said conducting line between said operatories and said vacuum source;
   said sludge trap means comprising: a first conduit element for dividing the flow in said conducting line so that fluids continue to move in a first path toward said vacuum source while sludge is separated from said first path into a second, downward, path; a downwardly extending, closed end, trap element connected to said first conduit element for receiving sludge flowing in said second path; and valve means disposed between said first conduit element and said trap element.

2. A system as recited in claim 1 wherein said first conduit element and said closed end, trap element are completely static structures.

3. A system as recited in claim 2 further comprising a no-hub coupling between said first conduit element and said valve means.

4. A system as recited in claim 3 wherein said valve means comprises a manually operated slide valve.

5. A system as recited in claim 2 wherein said trap element comprises a length of plastic pipe capped at the bottom end thereof.

6. A system as recited in claim 2 wherein said first conduit element comprises a sanitary tee.

7. A system as recited in claim 6 further comprising liquid and slurry separating means disposed between said vacuum source and said sludge trap means, and connected to a drain, for draining liquids and slurries from said fluid conducting line before said vacuum source.

8. A system as recited in claim 7 wherein said liquid separating means comprises a plurality of generally parallel and vertical tubular elements each having a cross-sectional area greater than the cross-sectional area of said fluid conducting line, and extending generally below said fluid conducting line, and operatively connected to a drain at the bottoms thereof.

9. A system as recited in claim 8 wherein said liquid separating means further comprises a plurality of sanitary tees each having an in-line inlet and outlet extending along said fluid conducting line, and an elbow outlet extending downwardly from said fluid conducting line, each of said tubular elements connected at the top thereof to an elbow outlet of one of said sanitary tees.

10. A dental vacuum system including a source 4 of vacuum operatively connected by a fluid conducting line to a plurality of operatories, and comprising liquid and slurry separating means disposed between said vacuum source and said operatories, and connected to a drain, for draining liquids and slurries from said fluid conducting line before said vacuum source;
    said liquid separating means comprising a plurality of generally parallel and vertical tubular elements each having a cross-sectional area greater than the cross-sectional area of said fluid conducting line, and extending generally below said fluid conducting line, and operatively connected to a drain at the bottoms thereof.

11. A system as recited in claim 10 wherein said liquid separating means further comprises a plurality of sanitary tees each having an in-line inlet and outlet extending along said fluid conducting line, and an elbow outlet extending downwardly from said fluid conducting line, each of said tubular elements connected at the top thereof to an elbow outlet of one of said sanitary tees.

12. A system as recited in claim 11 further comprising a common drain valve operatively connected between the bottoms of said tubular elements and a drain, and connected to said tubular elements by a quick disconnect coupling.

13. A system as recited in claim 10 wherein the fluid conducting line and tubular elements are circular in cross section, and wherein four tubular elements are provided, each having a diameter about twice the diameter of said fluid conducting line.

14. A system as recited in claim 12 wherein said common drain valve is lower than the rest of said separating means and further comprising an inner cross-sectional area reduction in pipes between said quick disconnect and said drain valve at an incline, so that free drainage is not impeded by said cross-sectional area reduction.

* * * * *